US007968052B2

(12) United States Patent
Mikkelsen et al.

(10) Patent No.: US 7,968,052 B2
(45) Date of Patent: Jun. 28, 2011

(54) DETECTION AND SUBSEQUENT REMOVAL OF AN APERTURE BLOCKAGE

(75) Inventors: Rune Funder Mikkelsen, Herlev (DK); Ulrik Darling Larsen, Lyngby (DK)

(73) Assignee: Chempaq A/S, Farum (DK)

( * ) Notice: Subject to any disclaimer, the term of this patent is extended or adjusted under 35 U.S.C. 154(b) by 295 days.

(21) Appl. No.: 12/067,065

(22) PCT Filed: Sep. 19, 2006

(86) PCT No.: PCT/DK2006/000514
§ 371 (c)(1),
(2), (4) Date: Aug. 29, 2008

(87) PCT Pub. No.: WO2007/033669
PCT Pub. Date: Mar. 29, 2007

(65) Prior Publication Data
US 2008/0314130 A1    Dec. 25, 2008

(30) Foreign Application Priority Data

Sep. 22, 2005 (DK) .................................. 2005 01323

(51) Int. Cl.
*G01N 15/12* (2006.01)
(52) U.S. Cl. ... 422/73; 422/68.1; 422/82.01; 422/82.02; 422/98; 73/61.56; 73/61.71; 73/61.73
(58) Field of Classification Search ................. 73/23.33, 73/31.01, 31.02, 31.05, 31.07, 865.5, 61.56, 73/61.71, 61.73; 422/55, 58, 61, 68.1, 73, 422/82.01, 82.02, 98
See application file for complete search history.

(56) References Cited

U.S. PATENT DOCUMENTS

| 3,259,891 | A |   | 7/1966  | Coulter et al. |
|-----------|---|---|---------|----------------|
| 3,963,985 | A |   | 6/1976  | Geldermans |
| 5,104,813 | A | * | 4/1992  | Besemer et al. ............. 436/179 |
| 5,230,866 | A | * | 7/1993  | Shartle et al. ............... 422/68.1 |
| 5,352,975 | A |   | 10/1994 | Ueno |

(Continued)

FOREIGN PATENT DOCUMENTS

EP    0559140 A1    9/1993

(Continued)

OTHER PUBLICATIONS

Kachel V: "Electrical Resistance Pulse Sizing: Coulter Sizing" Flow Cytometry and Sorting, Wiley-Liss, US, 1990, pp. 45-80, XP008023642.

*Primary Examiner* — David A. Rogers
(74) *Attorney, Agent, or Firm* — Volentine & Whitt, PLLC

(57) ABSTRACT

An apparatus which enables characterization of particles suspended in a liquid includes a housing with a mixing chamber and a collection chamber separated by a wall containing an aperture for passage of particles between, the mixing chamber and the collection chamber, the mixing chamber further containing a mixing member, a first electrode in the mixing chamber and a second electrode in the collection chamber for conduction of an electrical current through the aperture, a processor that is adapted for controlling the measurement sequence of the apparatus and detecting possible blockage of the aperture by detecting extended duration of the electrical pulse caused by the blocking particle, and upon detection of a blockage, reversing the liquid flow while mixing in the mixing chamber for removal of the blocking particle, and restarting particle counting.

6 Claims, 7 Drawing Sheets

U.S. PATENT DOCUMENTS

| | | | |
|---|---|---|---|
| 5,506,673 A | | 4/1996 | Kosaka et al. |
| 5,623,200 A | * | 4/1997 | Ogino .......................... 324/71.4 |
| 5,804,022 A | * | 9/1998 | Kaltenbach et al. .......... 156/257 |
| 6,387,328 B1 | * | 5/2002 | Berndtsson ..................... 422/73 |
| 6,418,802 B1 | | 7/2002 | Wood |
| 7,312,085 B2 | * | 12/2007 | Chou et al. ...................... 436/43 |
| 2003/0095897 A1 | * | 5/2003 | Grate et al. ................... 422/186 |
| 2006/0269446 A1 | * | 11/2006 | Gilbert et al. .................. 422/58 |
| 2008/0194508 A1 | * | 8/2008 | Christensen et al. ........... 514/44 |

FOREIGN PATENT DOCUMENTS

| | | |
|---|---|---|
| EP | 0652428 A1 | 5/1995 |
| NL | 7206329 A | 7/1972 |
| WO | 03104772 A | 12/2003 |

\* cited by examiner

DETECTION AND SUBSEQUENT REMOVAL OF AN APERTURE BLOCKAGE

CROSS REFERENCE TO RELATED APPLICATIONS

This application is the national phase under 35 U.S.C. 371 of PCT International Application No. PCT/DK2006/000514 which has an international filing date of Sept. 19, 2006, and also claims priority under 35 U.S.C. 119 to Danish application PA 2005 01323 filed on Sept. 22, 2005, which applications are hereby incorporated by reference in their entirety for all purposes as if fully set forth herein.

The present invention relates to a particle characterisation apparatus in which particles suspended in a liquid are passed through an orifice (called the aperture), in principle one by one, to enable the characterisation of the particles, for instance by Coulter counting.

It is well-known that particles suspended in an electrolytic liquid while travelling through a small aperture can be characterised with respect to size, concentration and conductivity by the use of an electrical impedance technique, widely known as the Coulter sizing (see V. Kachel, "Electrical Resistance Pulse Sizing: Coulter Sizing", Flow Cytometry and Sorting, Second Edition, pp. 45-80, 1990 Wiley-Liss).

Counting and sizing of panicles by the impedance principle is an internationally approved method fiat is being used in most haematology-analysers for counting blood cells. The method is based on measurable changes in the electrical impedance produced by non-conductive particles in an electrolyte. A small opening, called the "aperture" or "orifice", connects two electrically isolated chambers, where electrodes have been provided to contact the electrolyte. The aperture restricts the electrical path, whereby a sensing zone is established for passage of the particles. In the sensing zone each particle will give rise to a displacement of the surrounding electrolyte, thus blocking part of the current path and giving rise to a voltage pulse. By this method several thousand particles per second can be characterised with high precision.

The Haematology analysers are used for counting and differentiating blood cells such as Thrombocytes (Blood platelets), Leucocytes (White blood cells) and Erythrocytes (Red blood cells). The Leucocytes (White blood cells) are divided into three subpopulations: Lymphocytes, Monocytes and Granulocytes. These subpopulations may be distinguished by cell size by recording the response to a DC current of a cell passing through the aperture. Furthermore, Granulocytes are also divided into three subpopulations: Eosinophils, Basophils and Neutrophils. These subpopulations may be distinguished by cell density by recording the response to a RF current of a cell passing through the aperture.

Information on the content of Erythrocytes, Leukocytes, their subpopulations and Thrombocytes is an important tool for the physician in order to diagnose different diseases and monitor treatment.

It is also well known that large particles with a size close to or exceeding the size of the aperture may block the aperture and cause a measurement to fail. A method of removing the blocking (or clogging) of an aperture is disclosed in U.S. Pat. No. 3,963,985 wherein high alternating electrical currents are used for making a blast removal (gas explodes) of the particle (debris).

SUMMARY OF THE INVENTION

It is an object of the present invention to provide a method and an apparatus for detection and subsequent removal of a blockage of an aperture.

According to a first aspect of the present invention the above-mentioned and other objects are fulfilled by a method of operating an apparatus for characterizing particles suspended in a liquid sample, comprising a housing with a mixing chamber and a collection chamber separated by a wall containing an aperture for passage of particles between the mixing chamber and the collection chamber, the method comprising the steps of detecting possible blockage of the aperture by detecting extended duration of the electrical pulse caused by the blocking particle,
mixing in the mixing chamber,
reversing the liquid flow for removal of the blocking particle, and
restarting particle counting.

According to a second aspect of the present invention the above-mentioned and other objects are fulfilled by an apparatus for characterizing particles suspended in a liquid sample, comprising a housing with a mixing chamber and a collection chamber separated by a wall containing an aperture for passage of particles between the mixing chamber and the collection chamber, the mixing chamber further containing a mixing member,
a first electrode in the mixing chamber and a second electrode in the collection chamber for conduction of an electrical current through the aperture,
a processor that is adapted for controlling the measurement sequence of the apparatus,
characterized in that
the processor is further adapted to
detect possible blockage of the aperture by detecting extended duration of the electrical pulse caused by the blocking particle, and upon detection of a blockage,
reverse the liquid few white mixing in the mixing chamber for removal of the blocking particle, and
restart particle counting.

The mixing member may be magnetic whereby the mixing member may be moved by an externally moving magnetic field for stirring of the liquid in the mixing chamber.

In another embodiment, the mixing member is driven by a motor mechanically coupled to the mixing member for stirring of the liquid in the mixing chamber.

In yet another embodiment, mixing is performed with bubbles, such as bubbles blown into the liquid in the mixing chamber.

The first and second electrodes may facilitate particle characterization utilizing the above-mentioned Coulter impedance principle, e.g. for counting and sizing of blood cells.

With the electrical impedance technique it is possible to resolve the particle volume from the measurement. By maintaining a constant current across the aperture, the recorded voltage pulse from particles displacing the electrolyte in the aperture will have a height proportional to the volume of the particle. This is due to the fact fiat particles can be considered non-conducting compared to the electrolyte. The electrical field (DC or RF) in the centre of the aperture is homogeneous, which is normally the case when the aperture diameter D is smaller than the length I of the aperture ($l/D>1$), the particle diameter d is to be considered small compared to the diameter of the aperture ($d<0.2*D$), only one particle passes through at a time and the particles are passed through the aperture along the length of the aperture.

Normally such apparatus is operated so that the flow through the aperture is into the collection chamber.

Preferably, the length of the aperture is from 1 µm to 1000 µm, for example about 50 µm. Desirably the length of the aperture is chosen such that only one particle will be present in the aperture at the time when detecting particles of from 0.1 µm to 100 µm in diameter. However, considerations to the homogeneity of the electrical field in the aperture may require a length of the aperture larger or equal to the aperture diameter. The counts, of which some may be simultaneous counting of two particles, can be corrected mathematically by implementing a statistical estimation. The aspect ratio of the aperture, (length or depth divided by diameter) is preferably from 0.5:1 to 5:1, more preferably from 1:1 to 3:1.

Preferably, the largest cross-sectional dimension of the aperture is from 5 µm to 200 µm, for example 10 µm to 50 µm.

In a preferred embodiment of the invention, the electrical current through the aperture is controlled to be substantially constant during particle counting. Thus, the detection of a blocked aperture may be based on monitoring the electrical voltage over the aperture. As a particle approaches the aperture, the voltage will start to increase as already described. If the particle is not passing through the aperture, the voltage will not be reset to the initial level. When such a shift in the voltage is detected, it is an indication of a particle blockage and the method for removing the blockage is performed.

In another embodiment, the voltage across the aperture is controlled to be substantially constant so that particles may be detected as negative going current pulses corresponding to the above-mentioned positive going voltage pulses.

The processor is further adapted to detect blockage of the orifice by calculation of a finite difference of an electrode signal, such as the current conducted by the first and second electrodes, or the voltage across the first and second electrodes, and comparing the calculated value with a threshold. When the absolute value of the calculated value exceeds the threshold, a blockage is detected.

The method of removing the blockage is based on hydrodynamic pressure and convection. Reversing the flow of the liquid in the aperture may push back the blocking particle. However, when the flow afterwards is changed to forward direction, the particle will often be caught in the aperture again. In order to prevent the particle from re-entering the aperture, a mixing, such as convective mixing, is initiated. Magnetic stir mixing or a similar mixing method may create the convective mixing.

Experiments show that most particles blocking an aperture are removed by the method according to the present invention. By performing the method according to the present invention, a 75% decrease of non-successful measurements was achieved.

It is an advantage of the present invention that the power consumption is low e.g. compared to the known blast-technique for removing a blockage of an aperture. For example the method according to the invention is available for utilisation in a small tabletop sized haematology analyzer with a small power supply, such as a battery driven device. Since the available power of such an apparatus is limited, the known blast-technique for removing blockages is less feasible. However, it is understood that the present invention may be applied in any type of apparatus with an aperture for passage of particles suspended in a liquid.

In WO 03/104772, a disposable cartridge for characterizing particles suspended in a liquid is disclosed. In particular, a self-contained disposable cartridge for single-use analysis, such as for single-use analysis of a small quantify of whole blood is disclosed. The self-contained disposable cartridge facilitates a straightforward measurement procedure, which can be performed by most people without any particular education. Furthermore, the apparatus used to perform the measurement with the cartridge is simple, maintenance free, and portable.

The method of the present invention may be incorporated into such an apparatus comprising a cartridge, preferably a disposable cartridge, and a docking station wherein the cartridge comprises the mixing chamber, the mixing member, the collection chamber, the electrodes, and the aperture, and the docking station for removably receiving the cartridge, comprises the processor and connectors for operational connection with the electrodes when the cartridge is received in the docking station.

The cartridge may further comprise a first port communicating with the collection chamber for causing a liquid flow through the aperture, while the docking station further comprises a first port for forming a gas connection with the first cartridge port when the cartridge is received in the docking station for application of a pressure causing a liquid flow through the aperture.

The cartridge may further comprise a second port communicating with the mixing chamber, and the docking station may further comprise a second port for forming a gas connection with the second cartridge port when the cartridge is received in the docking station for application of a pressure causing a liquid flow in the cartridge, such as a liquid flow into the mixing chamber.

Generally, it is preferred that all necessary electrical and fluid connections between toe cartridge and the docking station can be established by fitting the cartridge into the decking station, preferably by a simple push fit.

Preferably, the cartridge is designed to be disposable after a single use. It is desirable that after use there is no need to clean the apparatus before it can be used in a new assay procedure with a new cartridge. Accordingly, escape of liquid from the cartridge at its entry into the docking station should be avoided. To this end the positioning of the aperture within the housing is such that a volume of liquid sufficient for the desired particle characterization can be drawn or pumped through the aperture without the liquid passing out of the housing. Generally, it should be possible to pass a volume of liquid, which is at least 0.1 ml to 10 ml, e.g. 0.5 ml, through the aperture whilst particle characterization measurements are being made with no liquid leaving the cartridge.

The invention will be further described and illustrated with reference to the exemplified embodiments illustrated in the accompanying drawings in which:

FIG. 1 is a cross sectional side view through the components of a disposable unit referred to as the cartridge, FIG. 2 schematically illustrates the flow-through sensor concept, FIG. 3 schematically illustrates an apparatus with a disposable cartridge and a docking station according to the invention, FIG. 4 schematically illustrates a blocked aperture, FIG. 5 is a plot of the voltage as measured during blockage of the aperture, FIG. 6 is a flowchart of a method according to the invention, FIG. 7 is a plot of the voltage during blockage including subsequent resettlement of the voltage by removal of the blockage, FIG. 8 is a plot of finite difference of the aperture voltage with threshold levels defining the status of the blocked aperture, and FIG. 9 is an exemplary haematology analyser according to the present invention.

With reference to FIG. 1, a disposable cartridge with a housing 85 for blood analysis comprises a liquid storage chamber 1 containing a liquid diluent 11, a first sampling member 2 positioned in the housing 85 for sampling a blood sample 8 and having a cavity 10 for receiving and holding the blood sample 8, the member 2 being movably positioned in relation to the housing 85 in such a way that, in a first position, the cavity 10 is in communication with a bore 90 for entrance of the blood sample 8 into the cavity 10 by capillary forces, and, in a second position, the cavity 10 is in communication with the liquid storage chamber 1 and a mixing chamber 3 for discharge of the blood sample 8 diluted by the liquid diluent 11 into the mixing chamber 3 that holds the mixing member 92 for stir mixing. The mixing chamber 3 is separated from a collection chamber 5 by a wall containing an aperture 59 for the passage of the blood sample 8 between the mixing chamber 3 and the collection chamber 5. The wall containing the aperture 59 constitutes a part of a flow-through sensor 4.

A volume metering arrangement is connected to the collection chamber comprising a volume metering chamber 6 substantially having the size of the volume to be measured during the measurement with two connecting channels 12, 13 of relatively diminutive internal volumes for registering liquid entry and exit by optical or electrical means. A channel 7 leads from the volume metering chamber 6 out to a first connection port 67 where a pressure can be applied, e.g. for causing a liquid flow through the aperture 59.

As shown to FIG. 2, the flow-through sensor 4 has a dividing wall 91 with a relatively narrow aperture 59 for the passage of particles suspended in liquid 60. The aperture serves as a sensing zone for detection and measurement of the individual cells. The aperture in the sensor may be formed as a count aperture for counting and sizing particles by an impedance method known as Coulter counting. Particles can be aspirated through the aperture by pressure driven flow in either direction. When a saline or other electrolytic liquid solution is added to the chambers, the two chambers will be electrically isolated from each other except for the route for current flow provided by the passage through the aperture 59.

As shown in FIG. 3, the chambers on each side of the flow through sensor have electrodes 34, 35 extending from an external terminal 61, 62 through the base wall of the disposable cartridge and into a configuration facing the inside of its respective chamber. The cartridge is placed in a docking station 66 in a portable apparatus in order to carry out the measurement. The docking station 66 has a cup shaped housing having a base 70 and a circumambient sidewall 71. In the base 70 there are respective spring loaded electrical connectors 64, 65 for contacting the terminals 61,62 of the cartridge automatically when the cartridge is received as a push fit into the docking station. There is also a conduit 68 passing through the base wall 70 aligned with the conduit 67 of the cartridge. Conduit 67 at its opening into the upper face of the wall 70 has a seal 69, such as e.g. and O-ring for forming a gas tight connection with the lower face of the base wall of the cartridge. A vacuum pump 72 is connected by a line 73 to the lower end of the conduit 68. In a modification of the apparatus, the vacuum pump 72 can be reversed so as to apply positive gas pressure to the conduit 68. Schematically indicated at 74 are the further conventional components of a coulter counter including the processor and further electronic circuitry and display equipment needed for the operation of the apparatus.

FIG. 4 is a cross section of a membrane or wail 93 with an aperture 97 blocked by a large particle 94. The electrodes 66 are connected to a receiver 99 for impedance particle counting. As the particle 94 closes in to the aperture 97 the voltage changes 95 for an extended period compared to the response 98 from the passage of a normal particle.

Figure 1:
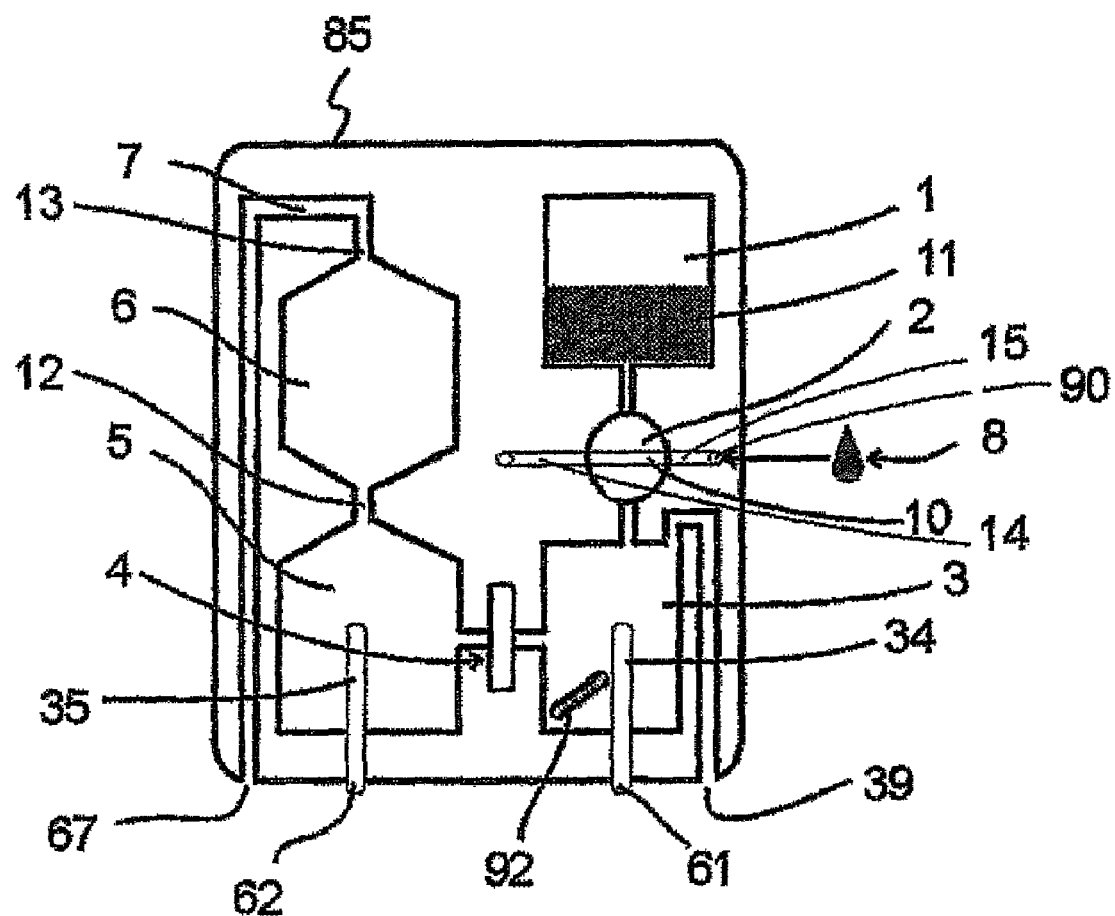
Figure 2:
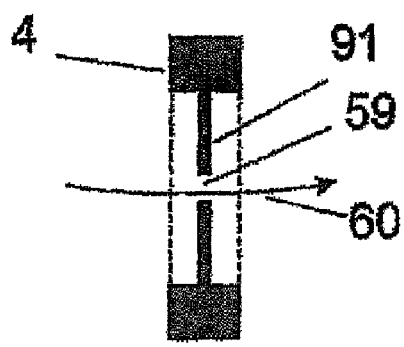
Figure 3:
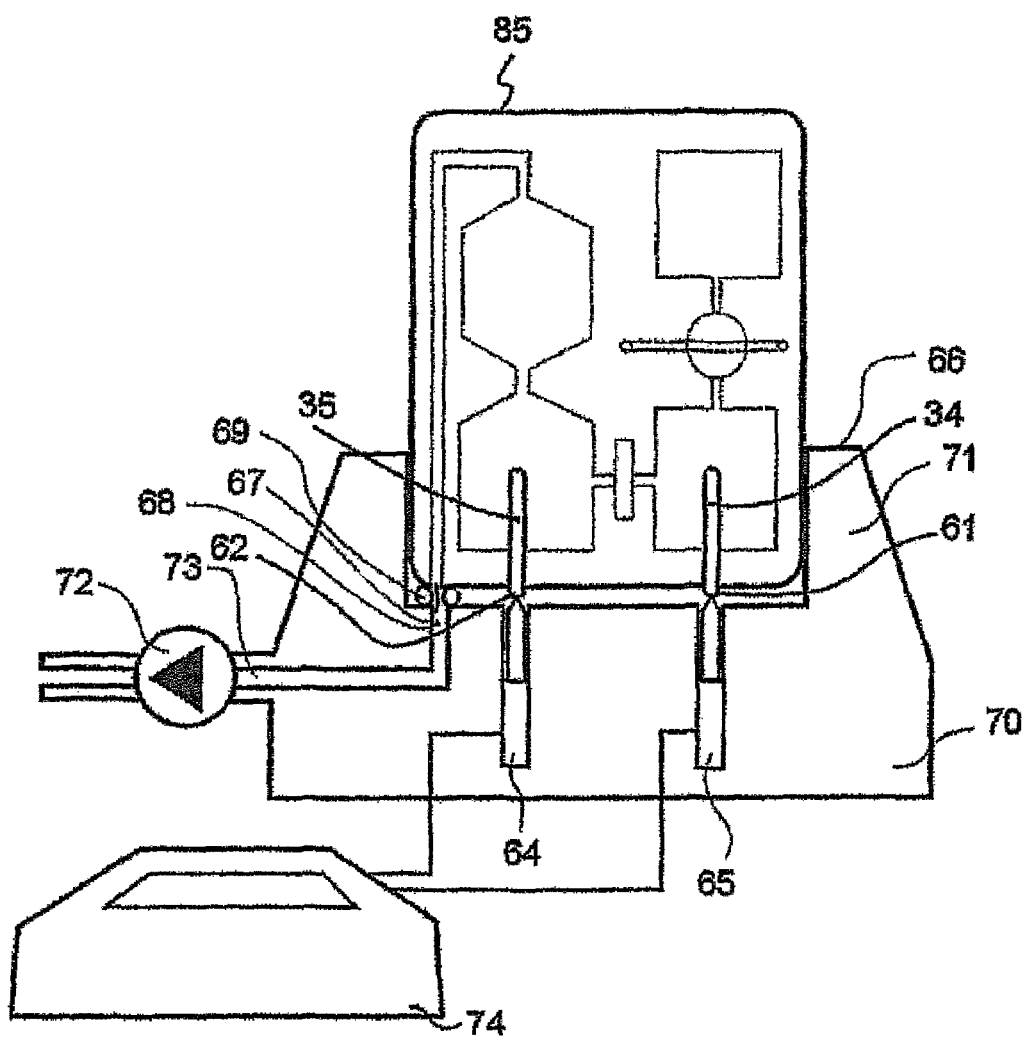
Figure 4:
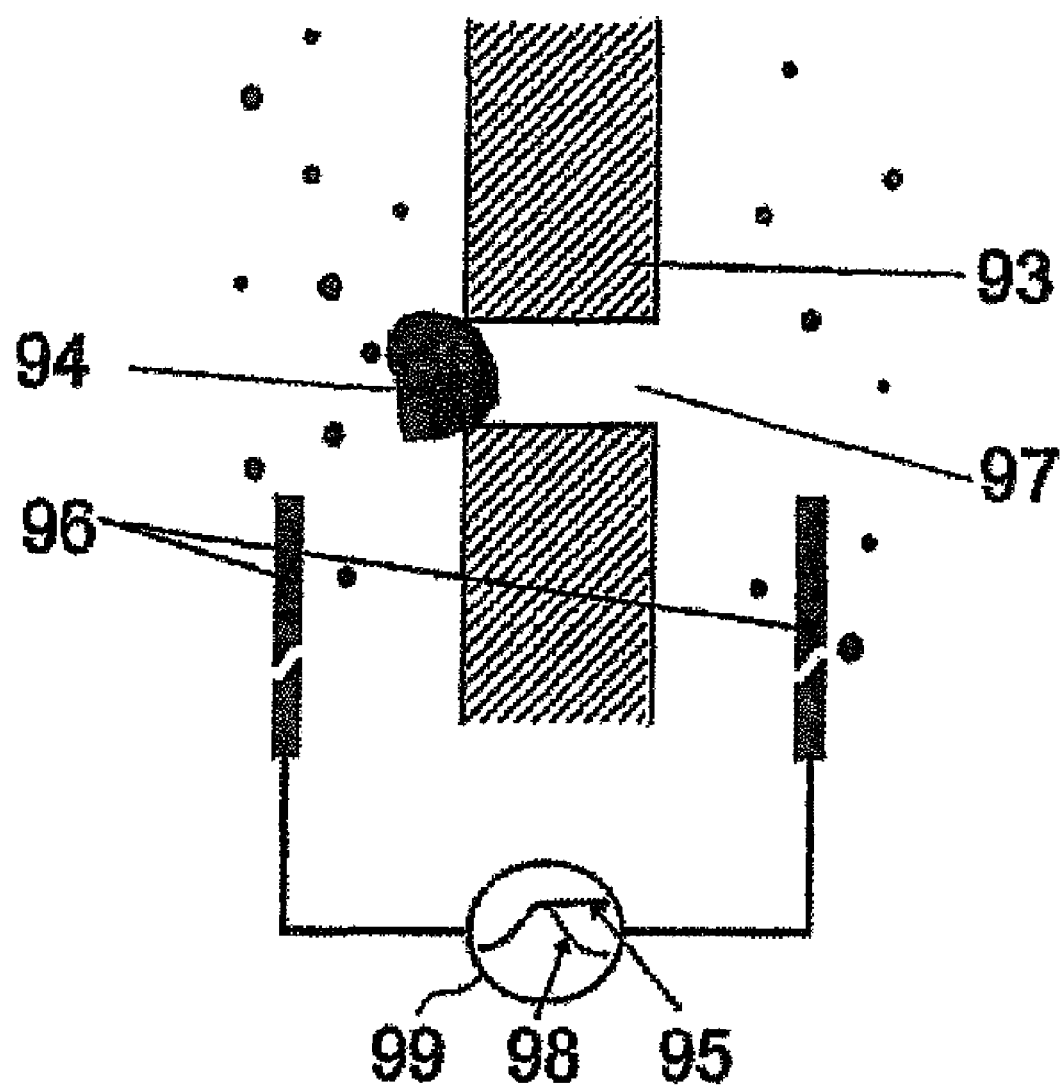

A typical timing of the monitoring and sampling of the aperture voltage (U) could be from 10 ms to 10 seconds and typically sampling each one second is preferred, if the time spacing is called x, the voltage at time x is denoted U(x). In FIG. 1 a monitoring of the voltage with a time resolution of 1 sample/sec is used.

One Way to detect a shift without looking at the actual level of the voltage is to look at finite differences, where the sampling data is the discrete values. A modified finite difference method could is expressed as $dU(X)=[U(X-3)+U(X-2)]/[U(X-1)+U(X)]$, where $dU(X)$ denotes the modified finite difference of the voltage at time x. When the voltage is stable the right side of this equation will be 1. When a shift in the voltage occurs (cf. FIG. 7) the finite difference will reflect this change (cf. FIG. 8) and by establishing thresholds (dotted lines in FIG. 8) for how much the finite difference can change in the normal situation, a shift caused by a particle can be detected. As the voltage of the aperture resettles to the initial value, the finite difference will detect this shift as well, which should not be regarded as a blockage. First after the voltage has been stable for a short period, the detection of a blockage can be initiated again.

Figure 6:
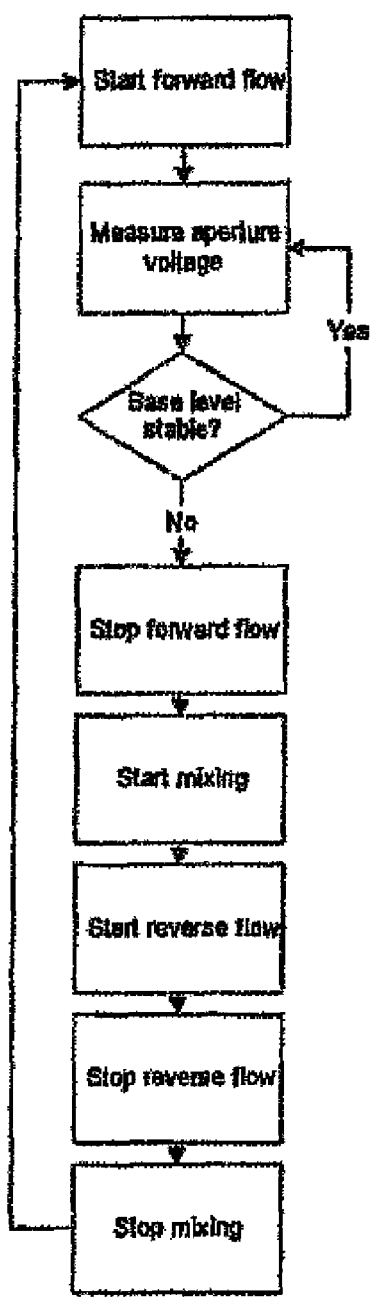
FIG. 6 is a flowchart of a method according to the present invention.
Figure 9:
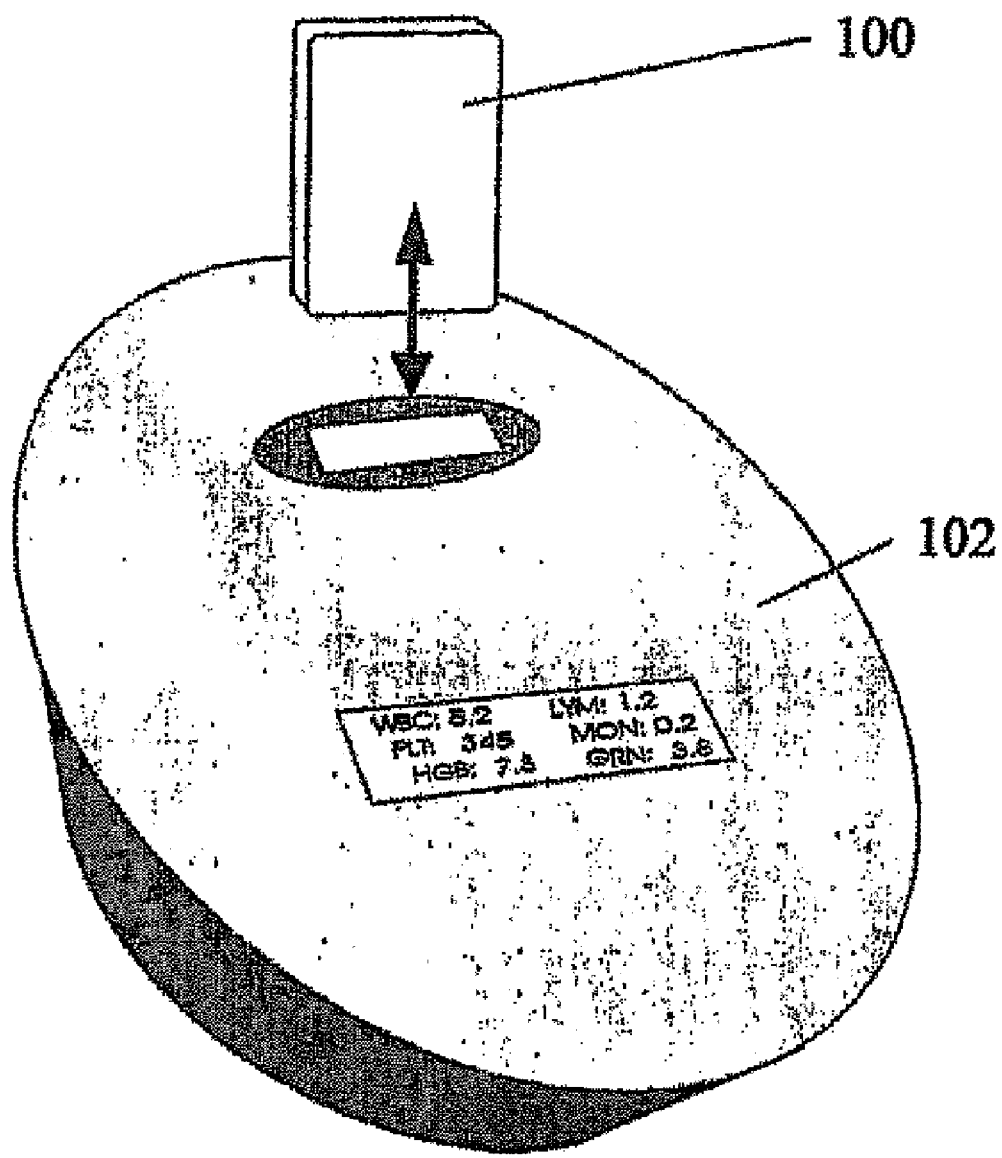

Reversing the flow and initiating a mixing removes the particle from the vicinity of the aperture. FIG. 6 illustrates an example of a sequence of how to perform this procedure in a specific analyzer apparatus (see FIG. 9). This apparatus comprises a disposable cartridge and a docking station for receiving the cartridge. The cartridge comprises a housing with a collection chamber bounded by a wall containing an aperture for the passage of the particles and having an inlet/outlet for connection to a source of positive or negative gas pressure, and electrodes for characterizing particles passing through the aperture fiat are connectable from outside the housing. The docking station comprises a first port for connection with a source of positive or negative gas pressure and forming a gas connection with the first cartridge port when the cartridge is received in the clocking station and electrical connectors for operative connection with the electrodes when the cartridge is received in the docking station. The processor controls the measurement cycle of the instrument. It transmits start and stop signals to the pulse height analyzer and to the valves for aspiration of the blood sample through the aperture. Hence, the voltage sampling, flow direction and monitoring of the measurement is performed by the processor.

Figure 7:
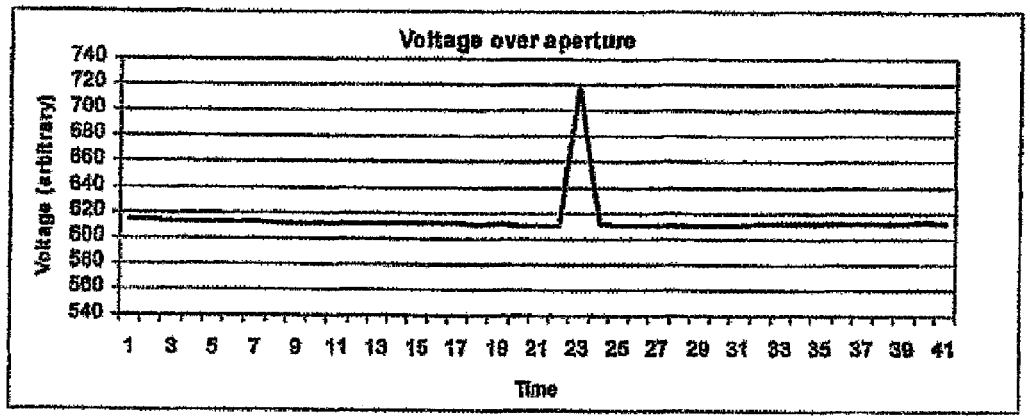

FIG. 7 is a recording of the voltage as a blocking occurs and is being removed again.

Figure 8:
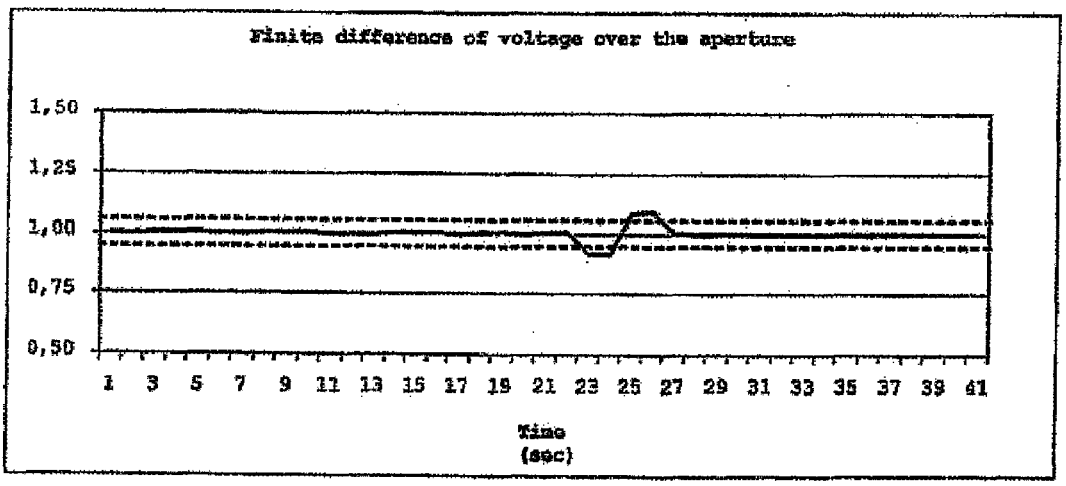

FIG. 8 is the modified finite difference of the recorded voltage used for monitoring for a potential blocking of the aperture. The dotted fines indicate threshold levels used for the identification of the blocking.

Figure 5:
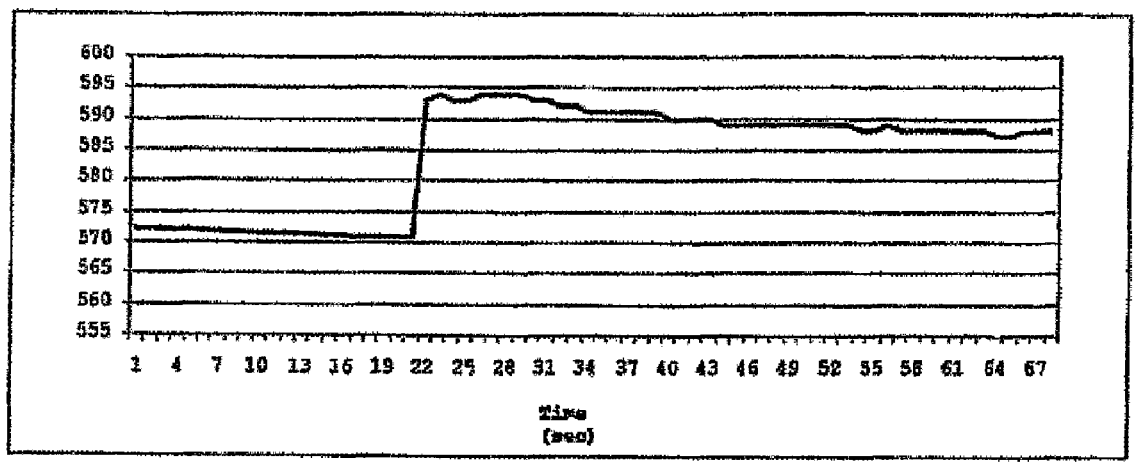
FIG. 5 is a recording of the extended voltage change arising from a particle blocking the aperture.

FIG. 5 is an example of a desktop apparatus 102 with a disposable cartridge 100 according to the present invention.

The invention claimed is:

1. An apparatus for characterizing particles suspended in a liquid sample, comprising a housing with
   a mixing chamber and a collection chamber separated by a wall containing an aperture for passage of particles between the mixing chamber and the collection chamber, the mixing chamber further containing a mixing member,
   a first electrode in the mixing chamber and a second electrode in the collection chamber for conduction of an electrical current through the aperture,
   a processor that is adapted for controlling a measurement sequence of the apparatus, characterized in that the processor is further adapted to detect possible blockage of the aperture during counting by detecting extended duration of an electrical pulse across the first and second electrodes caused by a blocking particle, and upon detection of a blockage, reverse liquid flow through the aperture while mixing in the mixing chamber for removal of the blocking particle, and restart particle counting.

2. An apparatus according to claim 1, wherein the mixing member is magnetic.

3. An apparatus according to claim 1, wherein the processor is further adapted to detect blockage of the aperture by calculation of a finite difference of an electrode signal and comparing the calculated finite difference with a threshold.

4. An apparatus according to claim 1, comprising a cartridge housing the mixing chamber, the mixing member, the collection chamber, the first and second electrodes, and the aperture, and a docking station for removably receiving the cartridge, the docking station comprising the processor and connectors for operational connection with the first and second electrodes when the cartridge is received in the docking station.

5. An apparatus according to claim 4, wherein the cartridge further comprises a first port communicating with the collection chamber for causing liquid flow through the aperture, and the docking station further comprises a second port for forming a gas connection with the first port when the cartridge is received in the docking station for application of a pressure causing liquid flow through the aperture.

6. A method of operating an apparatus for characterizing particles suspended in a liquid sample, the apparatus comprising a housing with a mixing chamber and a collection chamber separated by a wall containing an aperture for passage of particles between the mixing chamber and the collection chamber, a first electrode in the mixing chamber, and a second electrode in the collection chamber, the method comprising the steps of detecting possible blockage of the aperture during counting by detecting an extended duration of an electrical pulse across the first and second electrodes caused by the blocking particle, mixing in the mixing chamber upon detecting the blockage, reversing the liquid flow for removal of the blocking particle during said mixing in the mixing chamber, and restarting particle counting.

* * * * *